United States Patent [19]

Monzyk

[11] Patent Number: 5,328,626
[45] Date of Patent: * Jul. 12, 1994

[54] N-ETHYL HYDROXAMIC ACID CHELANTS

[75] Inventor: Bruce F. Monzyk, Maryland Heights, Mo.

[73] Assignee: Met-Tech Systems, Ltd., Burlington, Canada

[*] Notice: The portion of the term of this patent subsequent to Dec. 29, 2009 has been disclaimed.

[21] Appl. No.: 890,882

[22] Filed: May 29, 1992

Related U.S. Application Data

[63] Continuation-in-part of Ser. No. 732,989, Jul. 19, 1991, Pat. No. 5,174,917.

[51] Int. Cl.$^5$ .......................... C09K 3/00; C22B 3/00; C21B 3/00
[52] U.S. Cl. ........................................ 252/60; 252/61; 562/621; 562/622; 554/61
[58] Field of Search ............ 252/60, 61, 180; 562/621, 622, 623; 260/404; 554/111

[56] References Cited

U.S. PATENT DOCUMENTS

| | | | |
|---|---|---|---|
| 3,821,351 | 6/1974 | Lucid | 423/9 |
| 4,604,407 | 8/1986 | Haslanger et al. | 514/575 |
| 4,741,887 | 5/1988 | Coleman et al. | 423/112 |
| 4,874,539 | 10/1989 | Huffman | 252/174.24 |
| 4,975,253 | 12/1990 | Monzyk et al. | 423/139 |
| 5,030,427 | 7/1991 | Monzyk | 423/112 |
| 5,174,917 | 12/1992 | Monzyk | 252/60 |

Primary Examiner—Prince Willis, Jr.
Assistant Examiner—J. Silbermann
Attorney, Agent, or Firm—Thomas E. Kelley; Mark F. Wachter

[57] ABSTRACT

N-ethyl alkanohydroxamic acids, where said alkyl group is a straight chain alkyl group of 8 to 10 carbon atoms, or a branched alkyl group of 8 to 18 carbon atoms, provided said alkyl group is not cyclic, useful as metal chelants for use in organic solvent extractant solutions such as kerosene to extract metals from aqueous solutions by forming complexes of the extracted metal with the N-ethyl hydroxamic acid. Metals can be stripped from complexes of N-ethyl hydroxamic acids at higher concentrations into lower strength acid stripping agents. The N-ethyl hydroxamic acid-containing organic solvent extraction solutions exhibit rapid phase separation from aqueous solutions, good hydrolytic stability and resistance to forming emulsions.

4 Claims, No Drawings

N-ETHYL HYDROXAMIC ACID CHELANTS

This is a continuation-in-part of application Ser. No. 07/732,989, filed Jul. 19, 1991 now U.S. Pat. No. 5,174,917. Disclosed herein are novel N-ethyl hydroxamic acids, methods of making them and using them as metal chelants.

BACKGROUND OF THE INVENTION

Hydroxamic acids can be represented by the structural formula $R_1C(O)N(OH)R_2$, where $R_1$ is typically hydrogen or a hydrocarbon radical such as an alkyl radical, a cycloalkyl radical or an aromatic radical and $R_2$ can be a hydrogen atom or a hydrocarbon radical such as an aromatic radical or an alkyl radical. As disclosed by Lucid in U.S. Pat. No. 3,821,351, Coleman et al. in U.S. Pat. No. 4,741,887 and Monzyk et al. in U.S. Pat. No. 4,975,253, such hydroxamic acids are useful as chelants for extracting metals, e.g. from an aqueous solution of a mixture of metals. Hydroxamic acids containing at least about 7 carbon atoms are especially suitable for metal extraction being substantially insoluble in aqueous solutions and highly soluble in industrial organic solvents, e.g. kerosene.

Many hydroxamic acids exhibit distinct extraction profiles within a narrow band of pH for different metal species that allows for selectivity during extraction and/or stripping of metals. In a typical application a kerosene solution of such hydroxamic acid intimately mixed with an aqueous solution of a mixture of metals which transfer from the aqueous phase into the organic phase as complexes of the hydroxamic acid. Specific metal species can be selectively stripped from the kerosene phase by mixing the metal-loaded extractant with a series of aqueous solutions having a pH matching the distinct extraction profile of each metal species. The commercial utility of such hydroxamic acids also depends to a large extent on their hydrolytic stability, i.e. the resistance of the hydroxamic acid to dissociate in the aqueous solutions into hydroxylamine and carboxylate species, e.g. at an extreme pH typically used for stripping complexed metal from the hydroxamic acid. Hydroxamic acids that are hydrolytically unstable, e.g. useful for only a single, or at most a few, extraction/stripping cycles, are essentially of no commercial utility. In this regard Coleman et al. have shown that hydrolytic stability of hydroxamic acids depends of the nature of the $R_2$ radical. For instance, hydroxamic acids having hydrogen or an aromatic radical such as a phenyl group are substantially hydrolytically unstable, especially when exposed to low pH aqueous solutions commonly used to strip metal from hydroxamic acid complexes. Coleman et al. also demonstrated superior hydrolytic stability for hydroxamic acids where the $R_2$ radical is an alkyl group, e.g. a methyl group; such hydroxamic acids are referred to in the following description of this invention as N-alkyl, e.g. N-methyl, hydroxamic acids.

SUMMARY OF THE INVENTION

Despite their hydrolytic stability it has been found that certain N-alkyl hydroxamic acids form viscous emulsions, or even solid pastes, in organic extractants at high metal loadings, e.g. 50% solutions in kerosene at room temperature. In my work to find hydroxamic acids capable of high metal loading in extractants, I have discovered that novel N-ethyl alkanohydroxamic acids have surprising and unexpected properties, as compared to N-methyl hydroxamic acids, e.g., they allow the production and use of extractant solutions that exhibit faster phase disengagement from aqueous mixtures, higher metal loadings without forming emulsions, more efficient stripping of cations that typically are more tightly bound by other hydroxamic acids and higher and longer term hydrolytic stability. Another aspect of this invention comprises extractant solutions containing N-ethyl alkanohydroxamic acids. Still another aspect of this invention comprises methods of extracting metals from aqueous solutions using organic extractants containing N-ethyl alkanohydroxamic acids.

DESCRIPTION OF PREFERRED EMBODIMENTS

Unless expressly stated otherwise, in the description and claims of this invention, percentages of components in solutions, e.g. hydroxamic acids in kerosene, are in weight percent of the solution; kinematic viscosities are reported in units of millimeters$^2$ per second ($mm^2/s$), equivalent to centistokes.

The N-ethyl alkanohydroxamic acids of this invention are preferably essentially water insoluble, where the alkyl group is a straight chain alkyl group of 8 to 10 carbon atoms, or a branched alkyl group of 8 to 18 carbon atoms, provided said alkyl group is not cyclic. Preferred N-ethyl alkanohydroxamic acids of this invention are selected from the group consisting of N-ethyl n-octanohydroxamic acid, N-ethyl 2-ethylhexanohydroxamic acid, N-ethyl n-nonanohydroxamic acid, N-ethyl n-decanohydroxamic acid, N-ethyl neodecano hydroxamic acid, N-ethyl neotridecanohydroxamic acid and N-ethyl isostearohydroxamic acid. An especially preferred N-ethyl alkanohydroxamic acid is N-ethyl n-decanohydroxamic acid.

The N-ethyl alkanohydroxamic acids of this invention exhibit the unexpectedly advantageous property of low kinematic viscosity when provided in high concentrations. For instance, 50 weight percent (%) solutions of the N-ethyl alkanohydroxamic acid in kerosene exhibit kinematic viscosity of less than 20 millimeters$^2$/second ($mm^2/s$) at room temperature, e.g. 23° C. Preferably such solutions will exhibit a kinematic viscosity of less than 18 $mm^2/s$ or lower, e.g. less than 15 $mm^2/s$. For instance, where the 50% solution of N-methyl n-decanohydroxamic acid in kerosene is a solid, the analogous solution of the N-ethyl n-decanohydroxamic acid has a kinemtic viscosity of about 15 $mm^2/s$. Specifically excluded from this invention are the N-ethyl cycloalkanohydroxamic acids such as N-ethyl naphthenohydroxamic acids (the naphtheno radical is any of a group of cylcic pentyl radicals) which, apparently due to the cyclic ring structure, provide high viscosity solutions, e.g. greater than 20 $mm^2/s$ in 50% kerosene solutions at 23° C.

This invention also provides methods of extracting metal from aqueous solutions comprising contacting said aqueous solution with an organic solvent solution containing an N-ethyl alkanohydroxamic acid to extract the metal into the organic solvent solution as a hydroxamic acid complex. After the extracted solutions are separated; the separated organic solvent solution is contacted with an aqueous stripping solution at a pH less than 5 or greater than 9 to strip the complexed metal from the hydroxamic acid into the aqueous stripping solution. A preferred organic solvent solution capable of high metal loading comprises kerosene and at least about 50% of an N-ethyl alkanohydroxamic acid of this invention.

These N-ethyl alkanohydroxamic acids of this invention can be prepared by reacting N-ethyl hydroxylamine with a carboxylic acid chloride, e.g. n-octanoyl chloride, 2-ethylhexanoyl chloride, n-decanoyl chloride, iso-stearoyl chloride and the like. The reaction can be effected, preferably at low temperatures, e.g. less than 20° C., by adding the carboxylic acid chloride simultaneously with a base, e.g. aqueous sodium hydroxide, to a solution of the N-ethyl hydroxylamine in organic solvent, e.g. tetrahydrofuran, methylene chloride, etc. The hydroxamic acid product can be purified by washing with weak aqueous acid solutions, e.g. 1% acetic acid, then stripping the organic solvent. Useful reaction conditions are disclosed in U.S. Pat. Nos. 3,821,351 and 4,741,887, incorporated herein by reference.

The organic metal extractant solutions of this invention comprise an N-ethyl alkanohydroxamic acid in an organic solvent which is substantially immiscible with water so as to allow phase disengagement of extractant solutions from aqueous metal-bearing feed streams. Suitable solvents include aliphatic and/or aromatic hydrocarbon solvents such as kerosene, hexane, toluene, naphtha, cyclohexane and proprietary hydrocarbon solvents such as Chevron ® Ion Exchange Solvent, Kerr-McGee's Kermac ® 470-B kerosene solvent and Kermac 400-500 naphtha solvent, and Exxon's Isopar M, D 80 and Norpar 13 solvents, and Solvesso ® 100 kerosene solvent. Refined kerosene-based solvents having high flash point and high levels of aliphatic components are commonly preferred for industrial metal recovery applications. Generally at least 2% of the N-ethyl alkanohydroxamic acid component will be present in the organic solvent, e.g. about 2% to 60%, generally about 10% to 35%. Depending on the organic radical constituting the precursor carboxylic acid, the amount of hydroxamic acid in the solvent may vary to provide extractant solutions with appropriate viscosity and performance characteristics, e.g. high metal loading and rapid phase disengagement without forming emulsions.

The extractant solutions may also contain commonly used additives such as branched or long chain aliphatic alcohols, e.g. isodecanol, or phosphate esters, e.g. tributylphosphate. Such additives serve to prevent formation of third phases when extractants are intimately mixed with aqueous metal-bearing solutions, aid in phase disengagement and/or increase extractant solubility in the solvent. Such additives may find utility in a various concentrations depending to a large degree on the components of the aqueous metal-bearing solutions, e.g. in amounts ranging from about 1 to 50 volume percent, commonly about 5 to 10 volume percent.

The methods of this invention comprise the use of N-ethyl alkanohydroxamic acid-containing extractant solutions to extract metal from aqueous metal-bearing solutions. Such methods comprise contacting, e.g. intimately blending, the aqueous solution with an organic solvent solution containing an N-ethyl alkanohydroxamic acid to extract metal species into the organic solvent solution as a complex of the hydroxamic acid. After such mixing the mixed liquids are allowed to disengage into an metal-depleted aqueous phase and a metal-enriched organic solvent phase. The phases of disengaged solutions are readily separated, e.g. by decanting. The separated organic solvent solution can be contacted with a aqueous stripping solution, e.g. again by intimately blending, to strip the metal from the hydroxamic acid complex and transfer the metal into the stripping solution.

Depending on the unique equilibrium extraction curves (commonly called extraction isotherms) which are readily determined for any combination of a particular hydroxamic acid and metal species, the pH of the stripping solution can be readily adjusted to selectively strip particular metal species from the organic solvent solution. Multiple contacting with stripping solutions of different pH can be used to effectively strip different metals from mixed metal hydroxamic acid complexes. The blending for the extracting and stripping can be effected by a variety of well-known unit operations, e.g. batch operations in decanter vessels or in continuous operations with countercurrent flow between an alternating series of stirred mixers and quiescent phase separators. Useful selective stripping solutions often have a pH less than 5 or greater than 9 to strip said complexed metal from the hydroxamic acid into said aqueous stripping solution. Preferred general stripping solutions include 10–20% sulfuric acid, 10% hydrochloric acid or acid blends such as 20% sulfuric/20% phosphoric acid.

Although extraction techniques are well known to practitioners in the art, several especially useful methods of increasing the purity of extracted metals are disclosed by Monzyk in U.S. Pat. No. 5,030,427, incorporated herein by reference.

Among the advantages of metal extraction operations using the N-ethyl alkanohydroxamic acids of this invention are that the higher metal extraction capacity allows for smaller sized equipment and/or higher throughput, that higher stripping efficiency allows more thorough stripping resulting in higher concentrations of metal in stripping solutions, that speed of disengagement allows for shorter residence time or smaller volume of phase separators, and that higher resistance to hydrolytic degradation provides more longer on-stream time without replenishing the hydroxamic acid chelant. These and other advantages of the N-ethyl alkanohydroxamic acids of this invention will be apparent from the following illustrative examples which are not intended to indicate any particular limitation of the true scope of this invention.

EXAMPLE 1

This example illustrates one method of preparing an N-ethyl alkanohydroxamic acid and an extractant according to this invention. N-ethyl decanohydroxamic acid was prepared by reacting n-decanoyl acid chloride with ethyl hydroxylamine. 5.68 moles each of decanoyl chloride (1179 ml) and sodium hydroxide (309 ml of 50% NaOH) were separately and simultaneously slowly added to a solution of 6.27 moles of N-ethylhydroxylamine in a mixture of 683 ml of water and 1 liter of tetrahydrofuran cooled to 15° C. The temperature of the reactant mixture was maintained at less than 20° C. When addition was completed, the mixture was stirred for 1 hour; then, the reactant mixture was allowed to separate into phases. The by product salt was removed with the aqueous phase. The organic phase was washed twice with 1 liter of 1% aqueous acetic acid. About 1180 g of N-ethyl n-decanohydroxamic acid product was recovered by vaporizing residual solvents under vacuum at 60° C. An extractant solution was prepared by mixing 19.26 g of N-ethyl n-decanohydroxamic acid with 131 g of a mixture of 95 volume percent kerosene (Kermac ® 470B kerosene—a high aliphatic, high flash point kerosene obtained from Kerr-McGee) and 5 volume percent isodecanol, providing a clear extractant solution having a density of 0.8 g/ml (EXTRACTANT A).

COMPARATIVE EXAMPLE 1

A prior art extractant solution was prepared by dissolving 18 g of N-methyl n-decanohydroxamic acid in a mixture of 132 g of 95 volume percent kerosene (Kermac ® 470B kerosene) and 5 volume percent isodecanol, providing a clear extractant solution having a density of 0.8 g/ml (EXTRACTANT B).

EXAMPLE 2

This example illustrates the utility of an N-ethyl alkanohydroxamic acid of this invention in extracting iron from aqueous solutions and the rapid phase disengagement of the extractant from aqueous solutions. A 62 ml volume of EXTRACTANT A was blended for 20 minutes with a 50 ml volume of an acidic aqueous iron solution (0.15M ferric nitrate and 0.1M nitric acid), pH 1. When blending was stopped, complete separation of the aqueous and organic phases was effected in 28 seconds.

COMPARATIVE EXAMPLE 2

A 63 ml volume of EXTRACTANT B (N-methyl decanohydroxamic acid) was blended for 20 minutes with a 50 ml volume of the acidic, aqueous iron solution according to Example 2. When blending was stopped, complete separation of the aqueous and organic phases required 120 minutes. The short disengagement time for phase separation of the extractant containing an N-ethyl alkanohydroxamic acid provides a significant commercial utility compared to the prohibitively long disengagement time for the extractant containing the N-methyl alkanohydroxamic acid.

EXAMPLE 3

This example further illustrates the utility of an N-ethyl hydroxamic acid of this invention in extracting iron from aqueous solutions and the rapid phase disengagement of extractant from aqueous solutions. The iron extraction procedure of Example 2 was repeated with the following modification: the pH of the aqueous iron solution was raised to 2.5 by addition of 10N sodium hydroxide solution and EXTRACTANT A was blended with the aqueous iron solution for 30 minutes. When blending was stopped, complete separation of the aqueous and organic phases was effected in less than 60 seconds. Over 99 percent of the iron was extracted from the aqueous solution.

COMPARATIVE EXAMPLE 3

The iron extraction procedure of Example 3 was repeated using EXTRACTANT B. When blending was stopped, the aqueous and organic phases were an emulsion that failed to separate.

EXAMPLE 4

This example illustrates the ability of an N-ethyl alkanohydroxamic acid extractant solution of this invention to be rapidly stripped of metal by strong acid stripping solutions containing high concentrations of stripped iron. Six 10 ml volumes of iron-loaded EXTRACTANT A from Example 2 were sequentially stripped of iron by blending with a single 10 ml volume of a 40% acid stripping solution containing 20 weight percent sulfuric acid and 20 weight percent phosphoric acid. Each 10 ml volume of iron-loaded EXTRACTANT A was blended with the 10 ml volume of stripping acid for 2 minutes, the phases were allowed to separate (phase disengagement was effected within 1-2 minutes) and were decanted. The concentration of iron in the stripping solutions was determined to be 1.3%, 2.8%, 4.3%, 5.4%, 7.1%, and 8.4% iron, respectively, after each contact with an EXTRACTANT A solution. Iron concentration in the stripping solution increased with each mixing with fresh extractant with no indication of saturation of the stripping solution.

In a similar experiment a 40% acid stripping solution was loaded to 14.1% iron from iron-loaded EXTRACTANT A.

COMPARATIVE EXAMPLE 4

Seven 10 ml volumes of iron-loaded EXTRACTANT B from Comparative Example 2 were sequentially stripped of iron by blending with a single 10 ml volume of a 40% acid stripping solution of Example 4. Each 10 ml volume of iron-loaded EXTRACTANT B was blended with the 10 ml volume of stripping acid for 2 minutes, the phases were allowed to separate (disengagement required 2-6 minutes) and were decanted. The concentration of iron in the stripping solutions was 1%, 1.8%, 2.6%, 3.3%, 4.7%, 5% and 5.3%, respectively, after each contact with an EXTRACTANT B solution.

A comparison of the results of Example 4 and Comparative Example 4 indicates that enhanced ability of N-ethyl decanohydroxamic acid to release complexed iron into 40% stripping acid containing at least up to 8.5% iron; the saturation level for stripping extractants of N-methyl decanohydroxamic acid appears to be about 5.5% in 40% stripping acid. This indicates that iron can be concentrated to at least a 55% higher level in the 40% acid stripping solutions when the extractant contains N-ethyl n-decanohydroxamic acid compared to N-methyl n-decanohydroxamic acid.

EXAMPLE 5

This example further illustrates the ability of an N-ethyl alkanohydroxamic acid extractant solution of this invention to be rapidly stripped of metal by weaker acid stripping solutions containing stripped iron. Six 10 ml volumes of iron-loaded EXTRACTANT A from Example 3 were sequentially stripped of iron by blending with a single 10 ml volume of a 10% sulphuric acid stripping solution. Each 10 ml volume of iron-loaded EXTRACTANT A was blended with the 10 ml volume of stripping acid for 2 minutes, the phases were allowed to separate (phase disengagement was effected within 3-5 minutes) and were decanted. The concentration of iron in the stripping solution was 1.3%, 2.2%, 2.8%, 3.4%, 3.3%, and 3.8%, respectively, after each contact with an EXTRACTANT A solution.

COMPARATIVE EXAMPLE 5

A 10 ml volume of the iron-loaded EXTRACTANT B from Comparative Example 2 was blended with a 10 ml volume of 10% sulfuric acid stripping solution. After 8 hours the phases had not separated.

A comparison with the results of Example 5 illustrates the enhanced ability of N-ethyl n-decanohydroxamic acid to release complexed iron into stripping solutions containing only sulfuric acid as compared to N-methyl n-decanohydroxamic acid.

EXAMPLE 6

This example illustrates the long term hydrolytic stability of N-ethyl alkanohydroxamic acids. 50 g of a solution of 10% by weight N-ethyl decano hydroxamic acid in Kermac ® 470B kerosene-based solvent containing 5% by volume isodecanol was blended continuously at room temperature with 50 g of a 40% acid stripping solution (according to Example 4). The hydroxamic acid was gradually hydrolyzed so that about of the hydroxamic acid remained after 60 days and about 60% remained after 180 days.

COMPARATIVE EXAMPLE 6

The procedure of Example 6 was repeated using N-methyl n-decanohydroxamic acid which was hydrolyzed so much that about 25% of the hydroxamic acid remained after 60 days.

EXAMPLE 7

This example illustrates the advantageous solubility characteristics of concentrated (50%) solutions of N-ethyl alkanohydroxamic acids. The hydroxamic acids indicated in Table 1 were mixed with equal parts by weight with kerosene at 23° C. When the mixture provided a solution, the kinematic viscosity was determined by flowing the solution at 23° C. through a Cannon-Fenske Routine Viscometer, size 150, obtained from Cannon Instrument Company, State College, Pa.

TABLE 1

| Hydroxamic Acid | Kinematic Viscosity |
|---|---|
| N-ethyl neodecano- | 11.3 mm$^2$/s (cSt) |

TABLE 1-continued

| Hydroxamic Acid | Kinematic Viscosity |
|---|---|
| N-ethyl n-decano- | 15.3 |
| N-ethyl isostearo- | 14.4 |
| Comparative Examples: | |
| N-methyl naphtheno- | 22 |
| N-methyl isostearo- | 18.5 |
| N-methyl n-decano- | solid paste |
| N-methyl naphtheno- | 28 |

While specific embodiments have been described herein, it should be apparent to those skilled in the art that various modifications thereof can be made without departing from the true spirit and scope of the invention. Accordingly, it is intended that the following claims cover all such modifications within the full inventive concept.

What is claimed is:

1. An organic metal extractant solution comprising a kerosense solvent and at least 50 weight percen N-ethyl alkanohydroxamic acid wherein said solution has a kinematic viscosity at 23° C. of less than 20 mm$^2$/s, wherein said alkyl group is a straight chain alkyl group of 8 to 10 carbon atoms, or a branched alkyl group of 8 to 18 carbon atoms, provided said alkyl group is not cyclic.

2. A solution according to claim 1 wherein said N-ethyl alkanohydroxamic acid is selected from the group consisting of N-ethyl n-octanohydroxamic acid, N-ethyl 2-ethylhexanohydroxamic acid, N-ethyl n-nonanohydroxamic acid, N-ethyl N-decanohydroxamic acid, N-ethyl neodecanohydroxamic acid, N-ethyl neotridecanohydroxamic acid and N-ethyl isostearohydroxamic acid.

3. A solution according to claim 2 wherein said N-ethyl alkanohydroxamic acid consists of N-ethyl n-decanohydroxamic acid.

4. N-ethyl N-decanohydroxamic acid.

* * * * *